(12) United States Patent
Marczyk

(10) Patent No.: US 10,653,418 B2
(45) Date of Patent: May 19, 2020

(54) SURGICAL INSTRUMENT WITH ARTICULATING TOOL ASSEMBLY

(71) Applicant: Covidien LP, Mansfield, MA (US)

(72) Inventor: Stanislaw Marczyk, Stratford, CT (US)

(73) Assignee: COVIDIEN LP, Mansfield, MA (US)

( * ) Notice: Subject to any disclaimer, the term of this patent is extended or adjusted under 35 U.S.C. 154(b) by 1014 days.

(21) Appl. No.: 15/049,383

(22) Filed: Feb. 22, 2016

(65) Prior Publication Data

US 2016/0166250 A1    Jun. 16, 2016

Related U.S. Application Data

(60) Continuation of application No. 13/331,139, filed on Dec. 20, 2011, now Pat. No. 9,706,994, which is a division of application No. 12/854,679, filed on Aug. 11, 2010, now Pat. No. 8,100,309, which is a continuation of application No. 12/345,167, filed on Dec. 29, 2008, now Pat. No. 7,815,090, which is a continuation of application No. 11/544,203, filed on Oct. 6, 2006, now Pat. No. 7,481,348.

(51) Int. Cl.
*A61B 17/068* (2006.01)
*A61B 17/072* (2006.01)
*A61B 17/29* (2006.01)
*A61B 17/32* (2006.01)

(52) U.S. Cl.
CPC ...... *A61B 17/07207* (2013.01); *A61B 17/068* (2013.01); *A61B 2017/2927* (2013.01); *A61B 2017/320052* (2013.01)

(58) Field of Classification Search
CPC ............ A61B 17/068; A61B 17/07207; A61B 2017/2927
See application file for complete search history.

(56) References Cited

U.S. PATENT DOCUMENTS

| | | | |
|---|---|---|---|
| 4,566,620 A | | 1/1986 | Green et al. |
| 4,643,542 A | * | 2/1987 | Gibson ............... F41G 1/38 359/424 |
| 4,728,020 A | | 3/1988 | Green et al. |

(Continued)

FOREIGN PATENT DOCUMENTS

| | | |
|---|---|---|
| EP | 0674876 A2 | 10/1995 |
| EP | 0807408 A1 | 11/1997 |
| WO | 03/030743 A2 | 4/2003 |

OTHER PUBLICATIONS

European Search Report for EP 07253836.6-2310 date of completion is Jan. 7, 2008 (10 pages).

(Continued)

*Primary Examiner* — Andrew M Tecco
(74) *Attorney, Agent, or Firm* — Carter, DeLuca & Farrell LLP

(57) ABSTRACT

A surgical stapling instrument including a handle portion, a body portion, an articulating tool assembly and an articulation mechanism is disclosed. The body portion extends distally from the handle portion. The articulation mechanism includes an articulation link for articulating the tool assembly, an articulation knob operatively coupled to the articulation link, wherein rotational motion of the articulation knob is translated into axial motion of the articulation link thereby articulating the articulating tool assembly.

14 Claims, 12 Drawing Sheets

(56) References Cited

U.S. PATENT DOCUMENTS

| | | | |
|---|---|---|---|
| 4,869,414 A | 9/1989 | Green et al. | |
| 5,312,023 A | 5/1994 | Green et al. | |
| 5,370,650 A | 12/1994 | Tovey et al. | |
| 5,383,888 A | 1/1995 | Zvenyatsky et al. | |
| 5,391,180 A | 2/1995 | Tovey et al. | |
| 5,403,342 A | 4/1995 | Tovey et al. | |
| 5,411,519 A | 5/1995 | Tovey et al. | |
| 5,417,203 A | 5/1995 | Tovey et al. | |
| 5,456,401 A | 10/1995 | Green et al. | |
| 5,482,197 A | 1/1996 | Green et al. | |
| 5,490,819 A | 2/1996 | Nicholas et al. | |
| 5,514,157 A | 5/1996 | Nicholas et al. | |
| 5,560,532 A | 10/1996 | DeFonzo et al. | |
| 5,575,799 A | 11/1996 | Bolanos et al. | |
| 5,578,048 A | 11/1996 | Pasqualucci et al. | |
| 5,607,450 A | 3/1997 | Zvenyatsky et al. | |
| 5,623,854 A * | 4/1997 | Snider | G05G 1/12 126/42 |
| 5,643,294 A | 7/1997 | Tovey et al. | |
| 5,645,209 A | 7/1997 | Green et al. | |
| 5,662,662 A | 9/1997 | Bishop et al. | |
| 5,700,275 A | 12/1997 | Bell et al. | |
| 5,704,534 A | 1/1998 | Huitema et al. | |
| 5,713,505 A | 2/1998 | Huitema | |
| 5,749,893 A | 5/1998 | Vidal et al. | |
| 5,766,205 A | 6/1998 | Zvenyatsky et al. | |
| 5,782,859 A | 7/1998 | Nicholas et al. | |
| 5,785,647 A | 7/1998 | Tompkins et al. | |
| 5,797,538 A | 8/1998 | Heaton et al. | |
| 5,797,959 A | 8/1998 | Castro et al. | |
| 5,823,066 A | 10/1998 | Huitema et al. | |
| 5,865,361 A * | 2/1999 | Milliman | A61B 17/07207 227/176.1 |
| 5,901,895 A * | 5/1999 | Heaton | A61B 17/07207 227/176.1 |
| 6,079,606 A * | 6/2000 | Milliman | A61B 17/07207 227/175.2 |
| 6,241,139 B1 * | 6/2001 | Milliman | A61B 17/07207 227/175.1 |
| 6,250,532 B1 | 6/2001 | Green et al. | |
| 6,306,085 B1 | 10/2001 | Farascioni | |
| 6,330,965 B1 * | 12/2001 | Milliman | A61B 17/07207 227/176.1 |
| 6,565,508 B2 | 5/2003 | Scirica et al. | |
| 6,619,529 B2 | 9/2003 | Green et al. | |
| 6,644,532 B2 | 11/2003 | Green et al. | |
| 6,669,073 B2 * | 12/2003 | Milliman | A61B 17/07207 227/175.2 |
| 6,709,389 B2 | 3/2004 | Farascioni | |
| 6,716,232 B1 | 4/2004 | Vidal et al. | |
| 6,877,647 B2 | 4/2005 | Green et al. | |
| 6,953,139 B2 * | 10/2005 | Milliman | A61B 17/07207 227/175.1 |
| 6,981,628 B2 | 1/2006 | Wales | |
| 7,087,071 B2 | 8/2006 | Nicholas et al. | |
| 7,143,924 B2 * | 12/2006 | Scirica | A61B 17/07207 227/175.2 |
| 7,278,563 B1 | 10/2007 | Green | |
| 7,303,107 B2 | 12/2007 | Milliman et al. | |
| 7,481,348 B2 | 1/2009 | Marczyk | |
| 7,640,830 B2 | 1/2010 | Bonis | |
| 7,815,090 B2 | 10/2010 | Marczyk | |
| 7,815,091 B2 | 10/2010 | Marczyk | |
| 7,891,534 B2 * | 2/2011 | Wenchell | A61B 17/07207 227/176.1 |
| 8,006,429 B2 | 8/2011 | Windauer | |
| 8,033,441 B2 | 10/2011 | Marczyk | |
| 8,100,309 B2 | 1/2012 | Marczyk | |
| 2001/0030219 A1 | 10/2001 | Green et al. | |
| 2002/0177874 A1 | 11/2002 | Nicholas et al. | |
| 2004/0108357 A1 * | 6/2004 | Milliman | A61B 17/07207 227/176.1 |
| 2004/0232201 A1 * | 11/2004 | Wenchell | A61B 17/07207 227/176.1 |
| 2005/0006430 A1 | 1/2005 | Wales | |
| 2005/0184124 A1 * | 8/2005 | Scirica | A61B 17/07207 227/176.1 |
| 2005/0184125 A1 | 8/2005 | Marczyk | |
| 2006/0069396 A1 | 3/2006 | Meade et al. | |
| 2006/0190034 A1 | 8/2006 | Nishizawa et al. | |
| 2006/0259071 A1 | 11/2006 | Nicholas et al. | |
| 2009/0266868 A1 * | 10/2009 | Wenchell | A61B 17/07207 227/180.1 |
| 2012/0091182 A1 | 4/2012 | Marczyk | |

OTHER PUBLICATIONS

European Search Report for EP 07253836-2310 dated Jan. 7, 2008 (10 pages).

* cited by examiner

SURGICAL INSTRUMENT WITH ARTICULATING TOOL ASSEMBLY

CROSS-REFERENCE TO RELATED APPLICATION

The present application is a continuation application of U.S. patent application Ser. No. 13/331,139 filed on Dec. 20, 2011, which is a divisional application of U.S. patent application Ser. No. 12/854,679 filed on Aug. 11, 2010 (now U.S. Pat. No. 8,100,309), which is a continuation application of U.S. application Ser. No. 12/345,167 filed on Dec. 29, 2008 (now U.S. Pat. No. 7,815,090), which is a continuation application of U.S. application Ser. No. 11/544,203 filed on Oct. 6, 2006 (now U.S. Pat. No. 7,481,348), the entire contents of all of which are hereby incorporated by reference herein.

TECHNICAL FIELD

The present disclosure relates to a surgical instrument having an articulating tool assembly. More particularly, the present disclosure relates to a surgical instrument which includes a mechanism for actuating an articulating surgical instrument, e.g., a linear stapler, from a non-articulated position.

BACKGROUND

Surgical instruments which include a tool assembly mounted on a distal end of a body portion of the surgical instrument for articulation are well known. Typically, such surgical instruments include articulation control mechanisms which allow an operator to remotely articulate the tool assembly in relation to the body portion of a surgical instrument to allow the operator to more easily access, operate on, and/or manipulate tissue.

Such articulating tool assemblies have become desirable, especially in the endoscopic surgical procedures. In an endoscopic surgical procedure, the distal end of a surgical instrument is inserted through small incisions in the body to access a surgical site. Typically, a appropriately sized cannula, e.g., 5 mm, 10 mm, etc., is inserted through the body incision to provide a guide channel for accessing the surgical site. Because it is desirable to provide small body incisions, i.e., less scarring, reduced trauma to the patient, faster healing time, the tolerances between the surgical instrument and the inner diameter of the cannula are small.

Conventional articulating tool tips have a limited range of motion mainly due to mechanical design limitations of actuating mechanisms. It is desirable to provide an articulating surgical instrument which includes an articulation mechanism that would provide a wider range of motion for the articulation tip.

SUMMARY

The present disclosure relates to a surgical stapling instrument. The surgical stapling instrument includes a handle portion including a movable handle, the movable handle being movable through an actuation stroke. The surgical instrument also includes a body portion extending distally from the handle portion and defining a first longitudinal axis and a disposable loading unit configured for releasable engagement with a distal end of the body portion. The disposable loading unit includes a proximal body portion and an articulating tool assembly defining a second longitudinal axis. The articulating tool assembly is disposed adjacent a distal end of the proximal body portion and is movable from a first position in which the second longitudinal axis is substantially aligned with the first longitudinal axis to at least a second position in which the second longitudinal axis is disposed at an angle to the first longitudinal axis. The instrument further includes an articulation mechanism including a second articulation link, an articulation knob mounted adjacent the handle portion and mechanically interfacing with an articulation spindle, the second articulation link having a proximal end operatively connected to the articulation knob and a distal end positioned adjacent the distal end of the body portion and operatively connected to the first articulation link, wherein rotational motion of the articulation knob is translated into lateral motion of the first and second articulation links thereby articulating the articulating tool assembly.

A surgical instrument is also contemplated by the present disclosure. The instrument includes a handle portion, a body portion extending distally from the handle portion and defining a first longitudinal axis and an articulating tool assembly defining a second longitudinal axis and having a proximal end. The articulating tool assembly is disposed at a distal end of the body portion and is movable from a first position in which the second longitudinal axis is substantially aligned with the first longitudinal axis to at least a second position in which the second longitudinal axis is disposed at an angle with respect to the first longitudinal axis. The instrument also includes an articulation mechanism coupled to the articulating tool assembly. The articulation mechanism includes a housing block configured to receive an articulation spindle rotatably housed within the housing block, wherein the articulation spindle defines a plurality of notches which are configured to mechanically interface with a plunger biased to engage the articulation spindle.

According to another embodiment of the present disclosure, a surgical instrument is provided. The instrument includes a handle portion, a body portion extending distally from the handle portion and defining a first longitudinal axis and an articulating tool assembly defining a second longitudinal axis and having a proximal end. The articulating tool assembly is disposed at a distal end of the body portion and is movable from a first position in which the second longitudinal axis is substantially aligned with the first longitudinal axis to at least a second position in which the second longitudinal axis is disposed at an angle with respect to the first longitudinal axis. The instrument also includes an articulation mechanism coupled to the articulating tool assembly. The articulation mechanism includes a housing block configured to receive an articulation spindle rotatably housed within the housing block, wherein the housing block and the articulation spindle are adapted to limit a rotational range of the articulation spindle.

The present disclosure also relates to a disposable loading unit configured for releasable engagement with a surgical instrument. The disposable loading unit includes a body portion, an articulating tool assembly and at least one coupling member.

DESCRIPTION OF THE DRAWINGS

Various embodiments of the presently disclosed surgical instrument are disclosed herein with reference to the drawings, wherein.

DETAILED DESCRIPTION OF EMBODIMENTS

Figure 1:
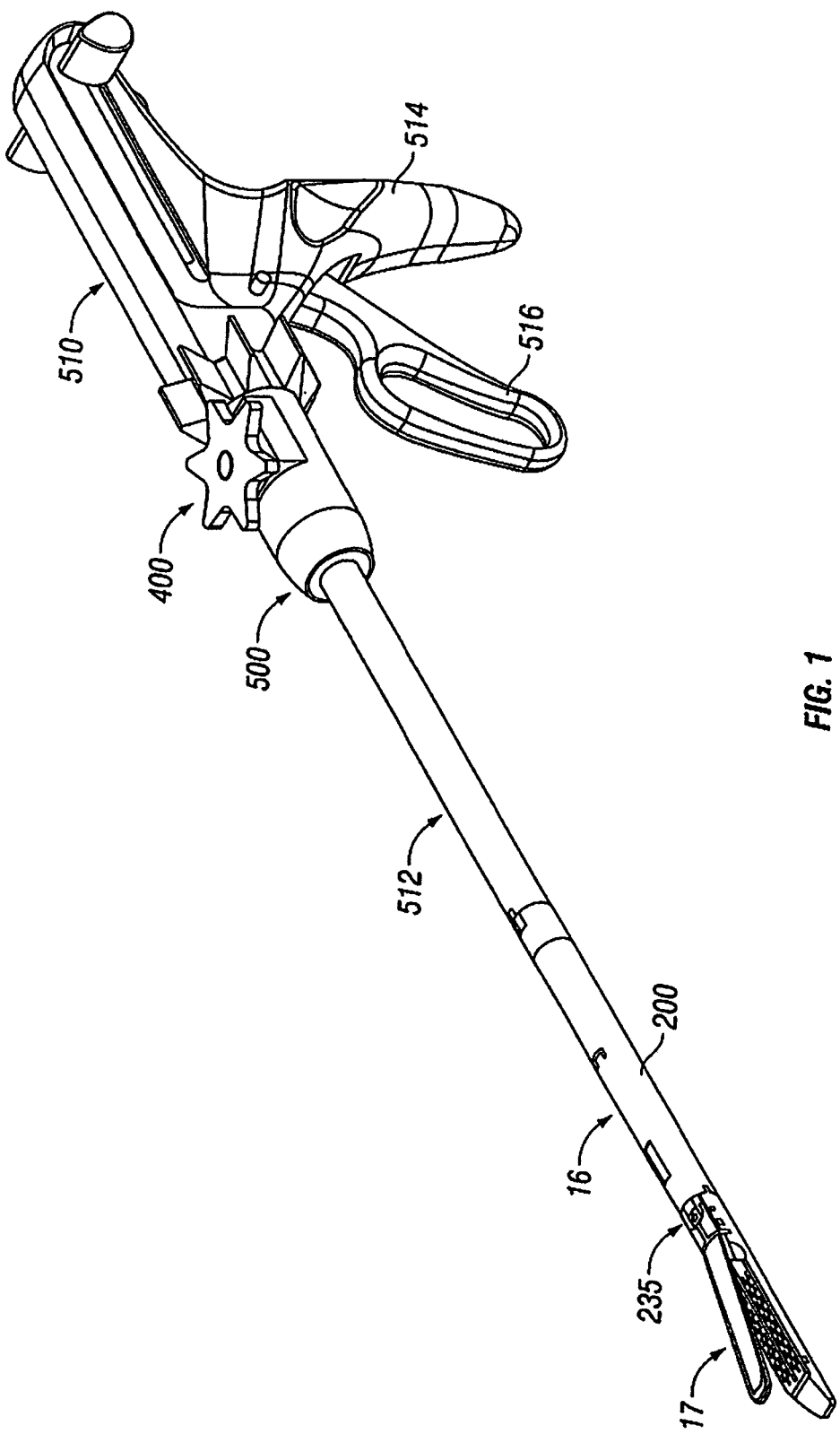
FIG. 1 is a side perspective view from the distal end of one embodiment of the presently disclosed surgical instrument with articulating tool assembly.

Embodiments of the presently disclosed surgical instrument and a disposable loading unit will now be described in detail with reference to the drawings, in which like reference numerals designate identical or corresponding elements in each of the several views.

Figure 10:
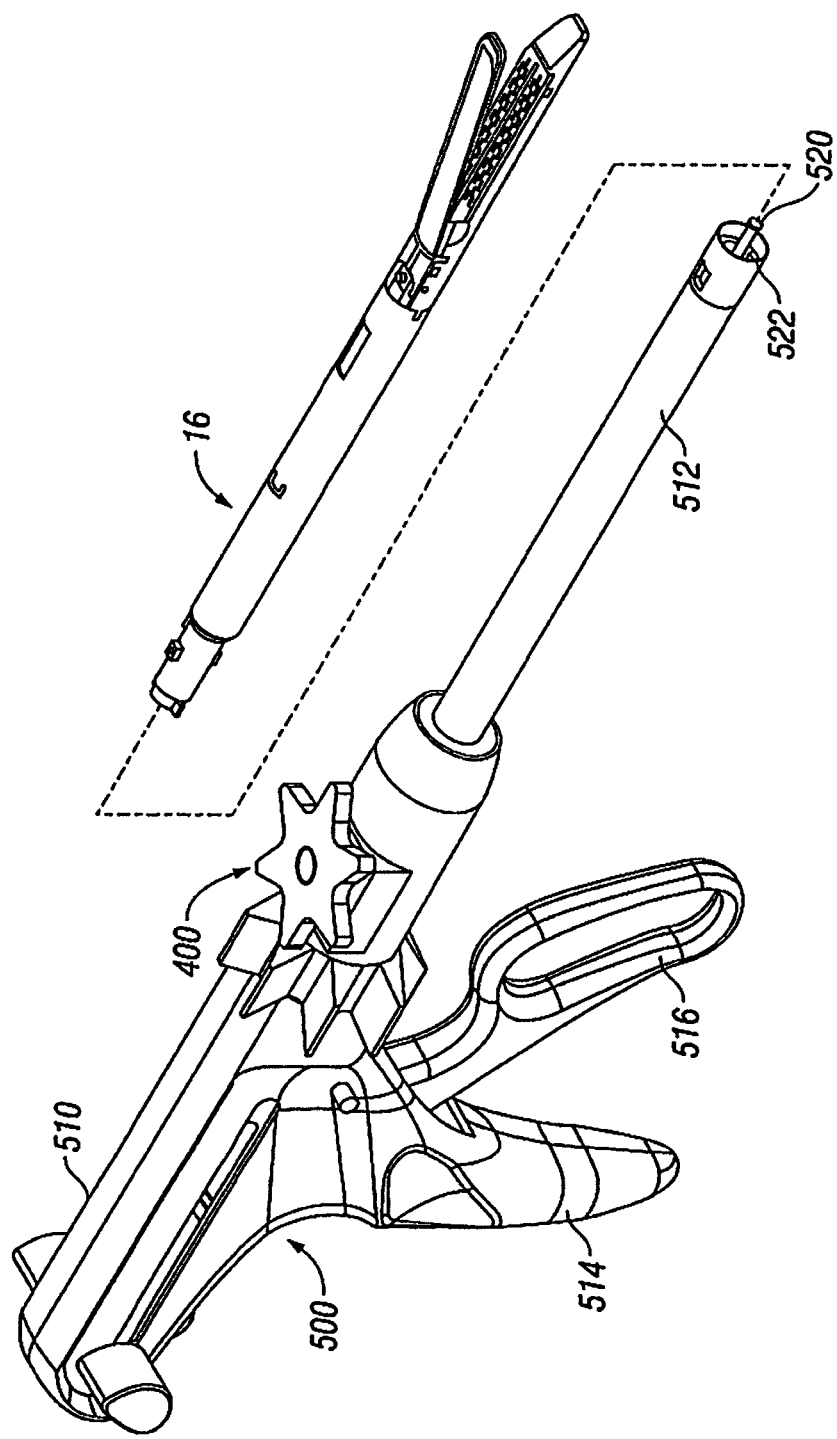
FIG. 10 is a side perspective view of the DLU and a surgical instrument shown in FIG. 1 prior to attachment of the DLU to the surgical instrument.

Referring to FIG. 1, surgical instrument 500 includes a handle portion 510, a body portion 512, and a disposable loading unit ("DLU") 16. Handle portion 510 includes a stationary handle 514 and a movable handle or trigger 516. Movable handle 516 is movable in relation to stationary handle 514 to advance a control rod 520 which projects from the distal end of body portion 512 (FIG. 10). Handle portion 510 and body portion 512 may be constructed in the manner disclosed in a commonly-owned U.S. Pat. No. 6,330,965 entitled "Surgical Stapling Apparatus" the contents of which are hereby incorporated herein in their entirety by reference. Alternately, other surgical instruments can be used with DLU 16 to perform endoscopic surgical procedures. The surgical instrument 500 also includes an articulation mechanism 400 for articulating a tool assembly 17 of the DLU 16.

Figure 1A:
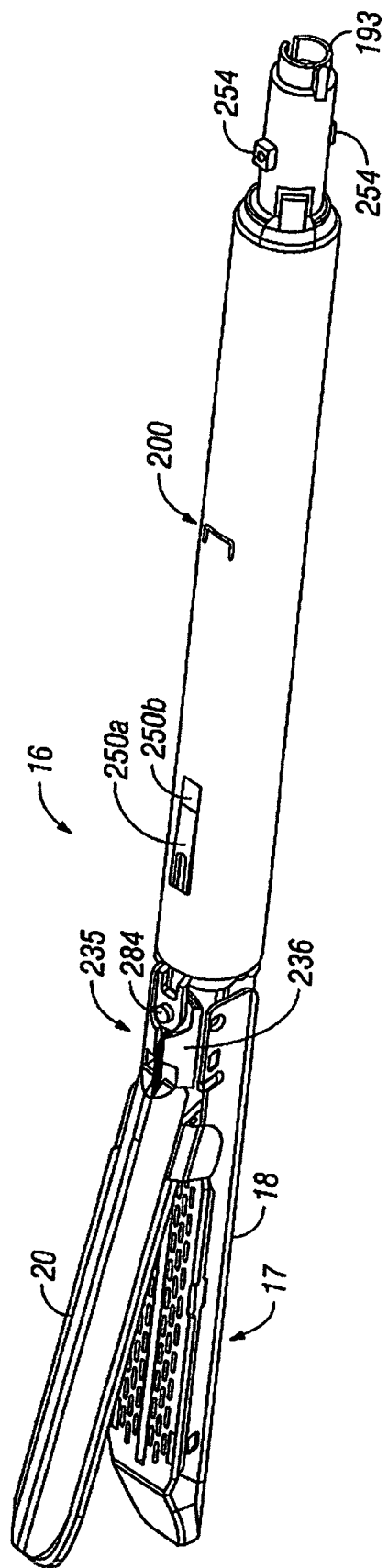
FIG. 1A is a side perspective view from the proximal end of a disposable loading unit (DLU) of the surgical instrument shown in FIG. 1 including the tool assembly.

Referring to FIGS. 1 and 1A, briefly, DLU 16 includes a tool assembly 17, a proximal body portion 200 and a mounting assembly 235. Body portion 200 has a proximal end adapted to releasably engage the distal end of a surgical instrument 500 (FIG. 10) in the manner to be discussed in detail below. Mounting assembly 235 is pivotally secured to a distal end of body portion 200 and is fixedly secured to a proximal end of tool assembly 17. Pivotal movement of mounting assembly 235 about an axis perpendicular to a longitudinal axis of body portion 200 effects articulation of tool assembly 17 between a non-articulated position in which the longitudinal axis of tool assembly 17 is aligned with the longitudinal axis of body portion 200 and an articulated position in which the longitudinal axis of tool assembly 17 is disposed at an angle to the longitudinal axis of body portion 200.

Figure 2:
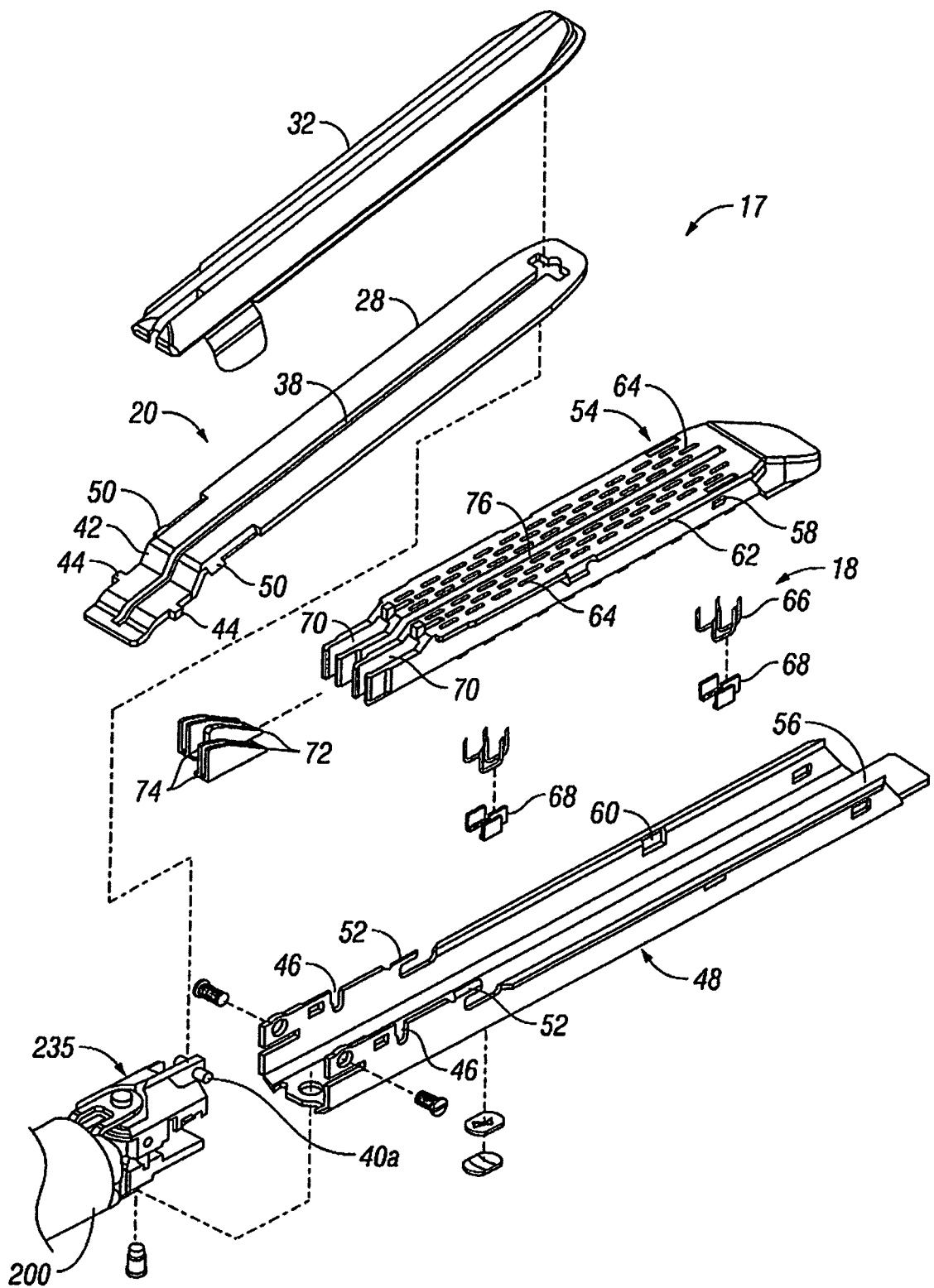
FIG. 2 is a side perspective view of the distal end of a mounting assembly and tool assembly, with parts separated, of the DLU of the surgical instrument shown in FIG. 1.
Figure 3:
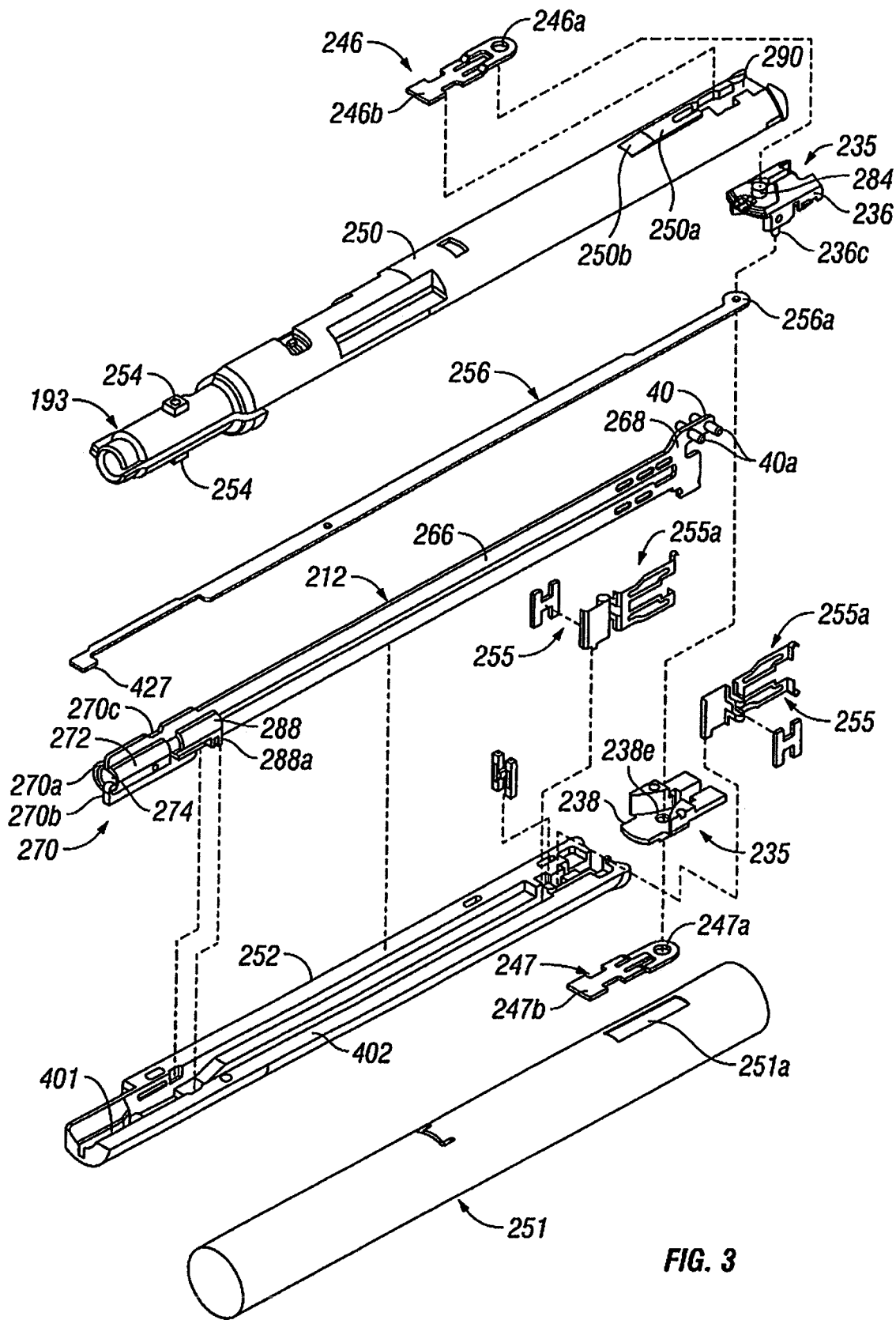
FIG. 3 is a perspective view of the mounting assembly and the proximal body portion of the DLU shown in FIG. 1A with parts separated.
Figure 4:
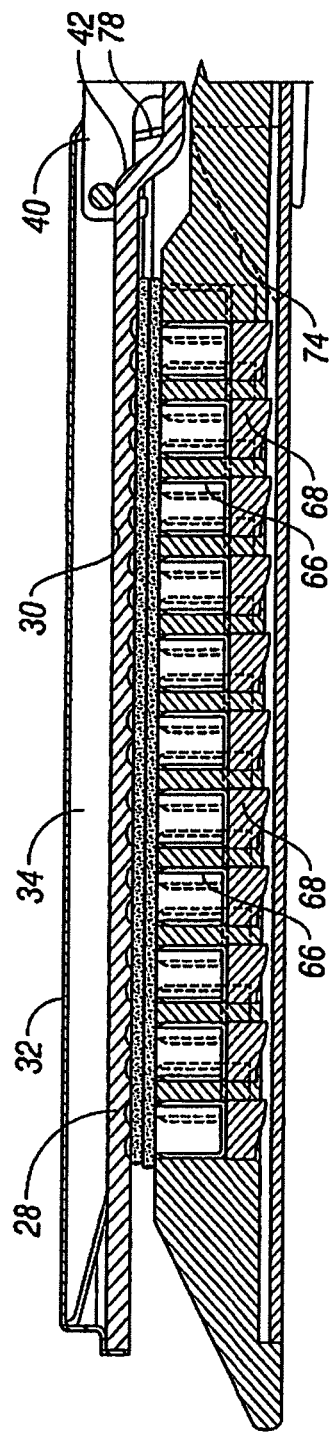
FIG. 4 is a side cross-sectional view of the tool assembly of the DLU shown in FIG. 1A.
Figure 5:
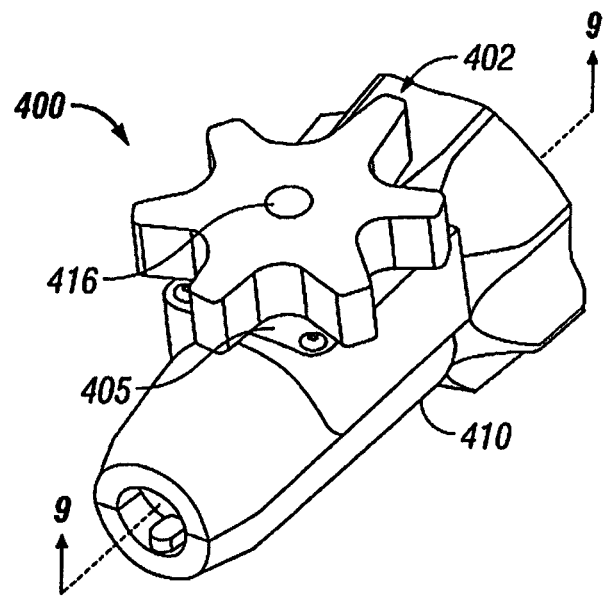
FIG. 5 is a side perspective view of an articulation mechanism of the surgical instrument shown in FIG. 1 according to the present disclosure.
Figure 6:
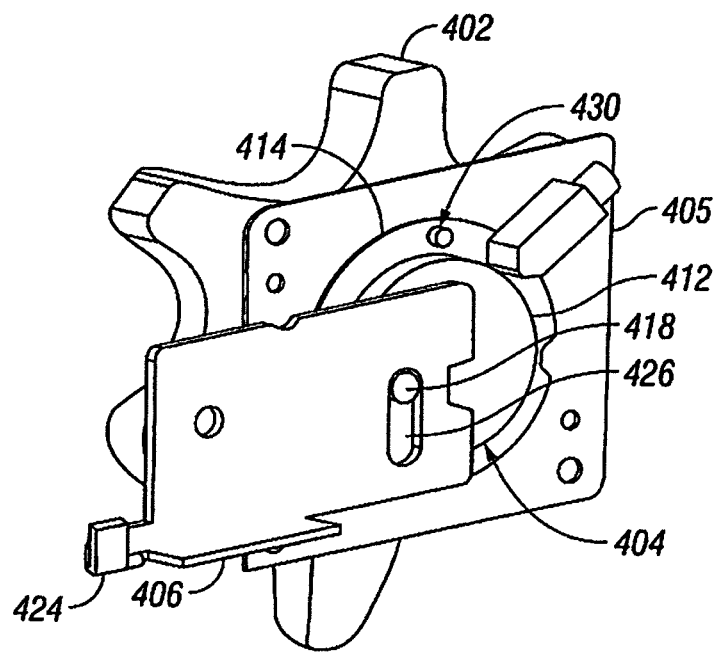
FIG. 6 is a perspective internal view of the articulation mechanism of FIG. 5 according to the present disclosure.
Figure 7:
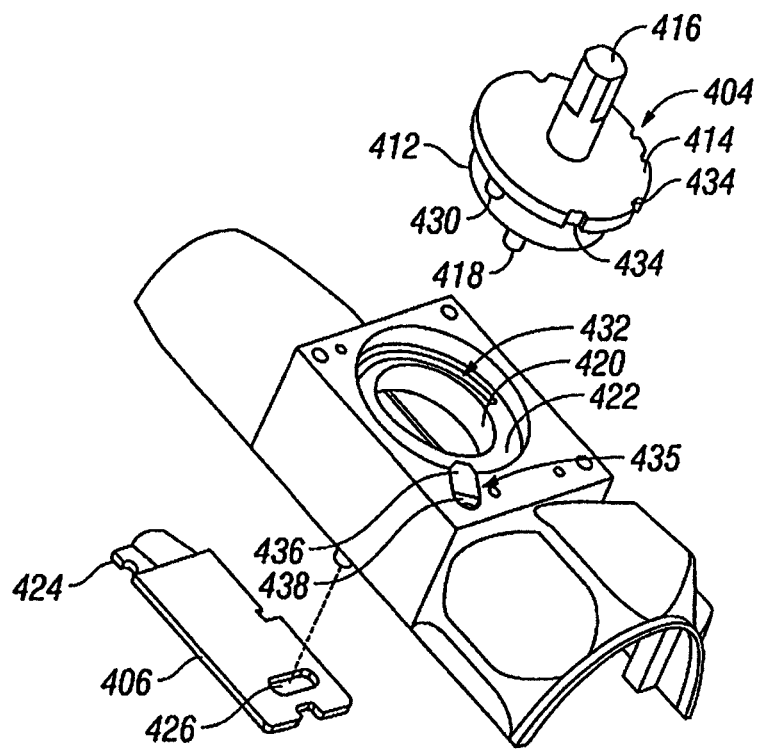
FIG. 7 is a perspective view with parts separated of the articulation mechanism of FIG. 5 according to the present disclosure.
Figure 8:
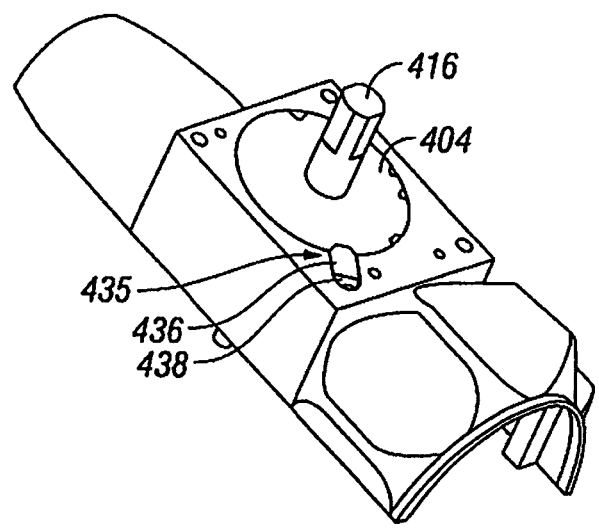
FIG. 8 is an external perspective view with parts assembled of the articulation mechanism of FIG. 5 according to the present disclosure.

Referring also to FIGS. 2-4, tool assembly 17 includes a cartridge assembly 18 and an anvil assembly 20. Anvil assembly 20 includes an anvil portion 28 having a plurality of staple deforming concavities 30 (FIG. 4) and a cover plate 32 secured to a top surface of anvil portion 28. Cover plate 32 and anvil portion 28 define a cavity 34 (FIG. 4) therebetween which is dimensioned to receive a distal end of a drive assembly 212 (FIG. 3). Cover plate 32 encloses the distal end of drive assembly 212 to prevent pinching of tissue during actuation of DLU 16. A longitudinal slot 38 extends through anvil portion 28 to facilitate passage of a retention flange 40 of drive assembly 212. A camming surface 42 formed on anvil portion 28 is positioned to engage a pair of cam members 40a supported on retention flange 40 of drive assembly 212 to effect approximation of the anvil and cartridge assemblies. A pair of pivot members 44 formed on anvil portion 28 are positioned within slots 46 formed in a cartridge assembly carrier 48 to guide anvil portion 28 between its spaced and approximated positions. A pair of stabilizing members 50 engage respective shoulders 52 formed on carrier 48 to prevent anvil portion 28 from sliding axially in relation to staple cartridge 54 as camming surface 42 is pivoted about pivot members 44.

Cartridge assembly 18 includes carrier 48 which defines an elongated support channel 56 which is dimensioned and configured to receive staple cartridge 54. Corresponding tabs 58 and slots 60 formed along staple cartridge 54 and elongated support channel 56, respectively, function to retain staple cartridge 54 at a fixed location within support channel 56. A pair of support struts 62 formed on staple cartridge 54 is positioned to rest on side walls of carrier 48 to further stabilize staple cartridge 54 within support channel 56.

Staple cartridge 54 includes retention slots 64 (FIG. 2) for receiving a plurality of staples or fasteners 66 and pushers 68. A plurality of laterally spaced apart longitudinal slots 70 extends through staple cartridge 54 to accommodate upstanding cam wedges 72 of an actuation sled 74 (FIG. 2). A central longitudinal slot 76 extends along substantially the length of staple cartridge 54 to facilitate passage of a knife blade 78 (FIG. 4). During operation of surgical stapler 10, drive assembly 212 abuts actuation sled 74 and pushes actuation sled 74 through longitudinal slots 70 of staple cartridge 54 to advance cam wedges 72 into sequential contact with pushers 68. Pushers 68 translate vertically along cam wedges 72 within fastener retention slots 64 and urge fasteners 66 from retention slots 64 into staple deforming cavities 30 (FIG. 4) of anvil assembly 20.

Referring to FIG. 3, mounting assembly 235 includes an upper mounting portion 236 and a lower mounting portion 238. A centrally located pivot member 284 extends from upper mounting portion 236 through a respective opening 246a formed in a coupling member 246. Lower mounting portion 238 includes a bore 238e for receiving a pivot member 284a (FIG. 3F). Pivot member 284a extends through bore 238e and second coupling member 246. Each of coupling members 246 and 247 include an interlocking proximal portion 246b, 247b configured to be received in grooves 290 formed in the distal end of an inner housing which is formed from upper and lower housing halves 250 and 252. Coupling members 246, 247 retain mounting assembly 235 and upper and lower housing halves 250 and 252 in a longitudinally fixed position in relation to each other while permitting pivotal movement of mounting assembly 235 in relation thereto.

Figure 3A:
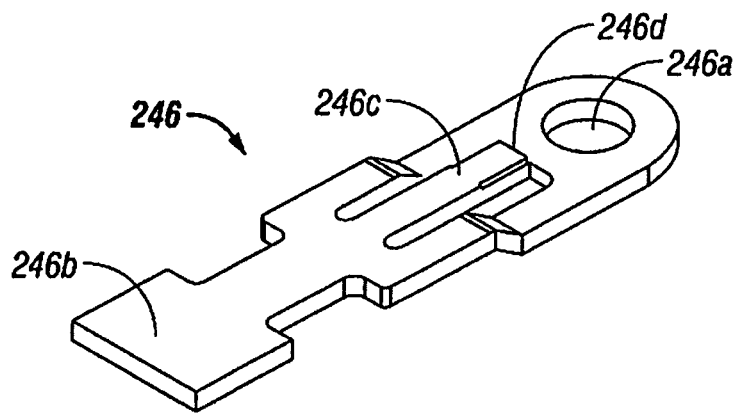
FIG. 3A is a side perspective view of a coupling member and retainer member of the surgical instrument shown in FIG. 1.
Figure 3B:
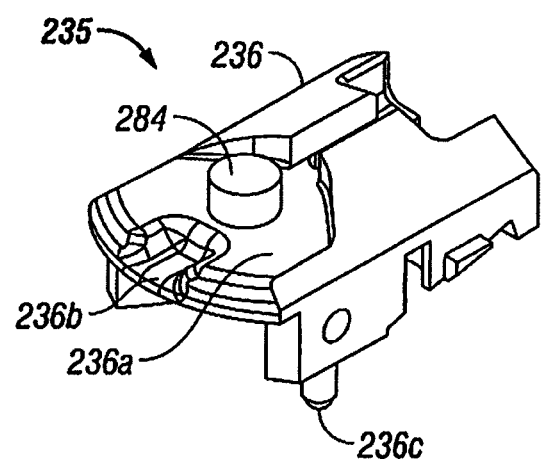
FIG. 3B is a side perspective view of an upper mounting portion of the mounting assembly of the DLU of the surgical instrument shown in FIG. 1.
Figure 3C:
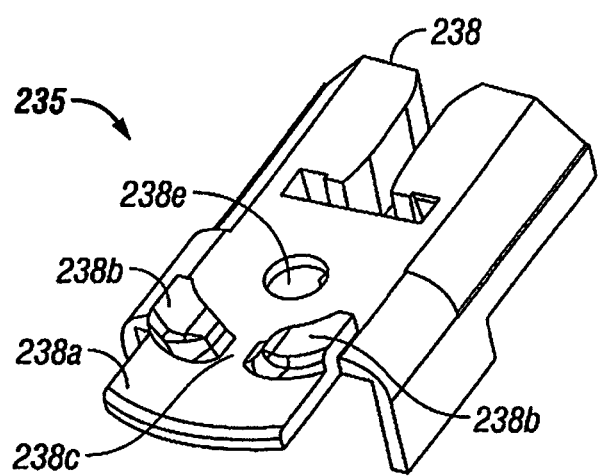
FIG. 3C is a side perspective view of a lower mounting portion of the mounting assembly of the DLU of the surgical instrument shown in FIG. 1.
Figure 3D:
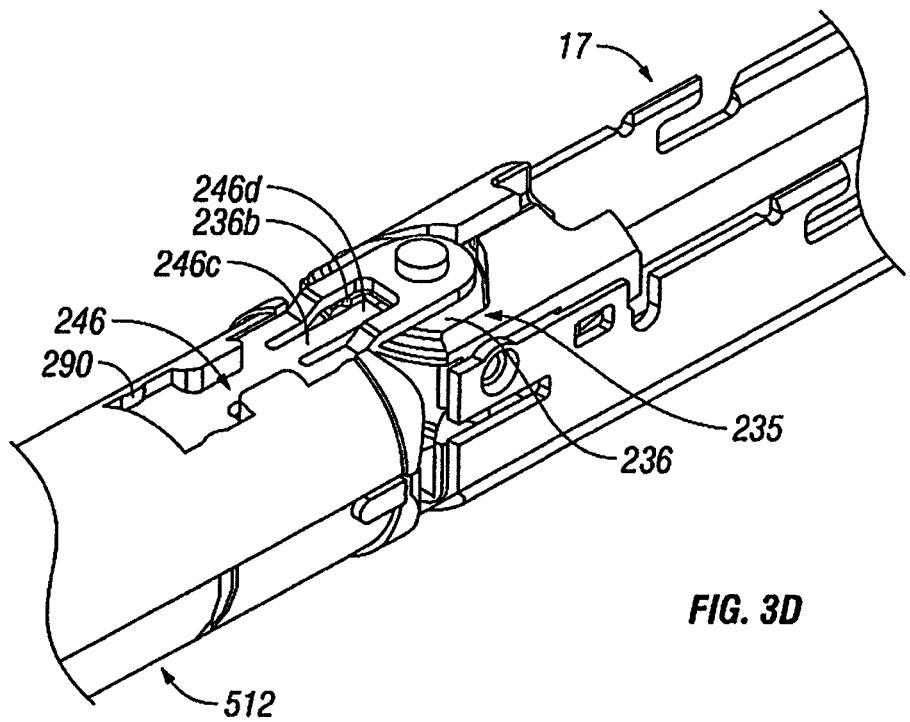
FIG. 3D is a side perspective view from above of the distal end of the proximal body portion, the mounting assembly and the proximal end of the tool assembly of the DLU of the surgical instrument with the tool assembly in its non-articulated position.

Referring to FIGS. 3A-3C, each coupling members 246, 247 includes a cantilevered spring arm 246c, 247c which has a distal end 246d positioned to engage mounting assembly 235. More specifically, upper mounting portion 236 includes a top surface 236a which includes a recess 236b dimensioned to receive distal end 246d of spring arm 246c of coupling member 246. Lower mounting portion 238 includes a bottom surface 238a having a pair of raised surfaces 238b which define a recess 238c which is dimensioned to receive spring arm 247c of coupling member 247. Alternatively, more than one recess may be formed in the upper and lower mounting portions of tool assembly 17, or a recess may be formed on either of the upper and lower mounting portions.

Figure 3E:
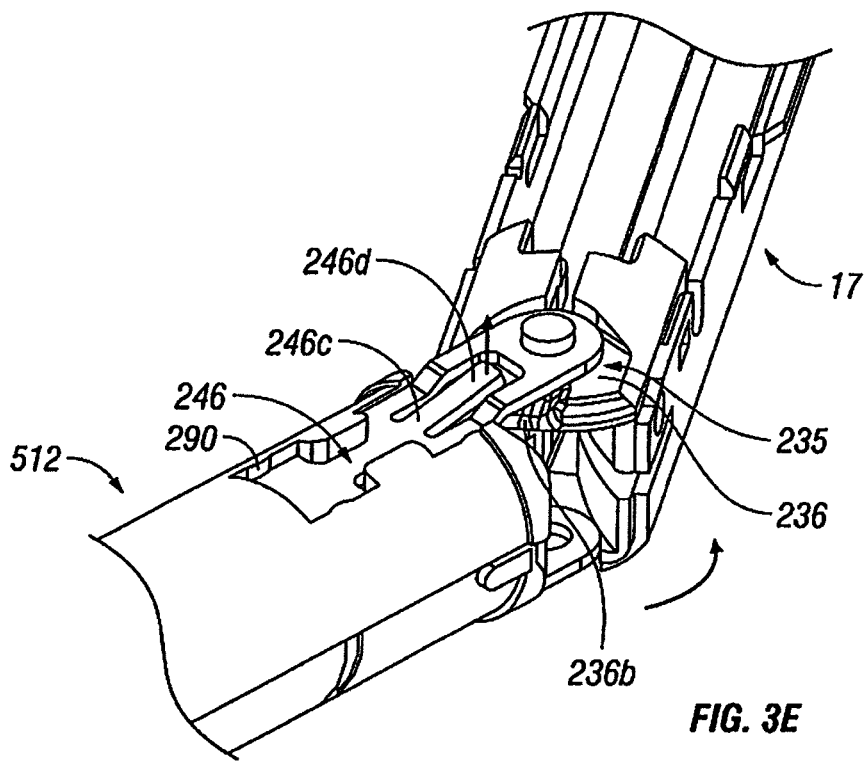
FIG. 3E is a side perspective view from above of the distal end of the proximal body portion, the mounting assembly and the proximal end of the tool assembly shown in FIG. 3D with the tool assembly moving to an articulated position.
Figure 3F:
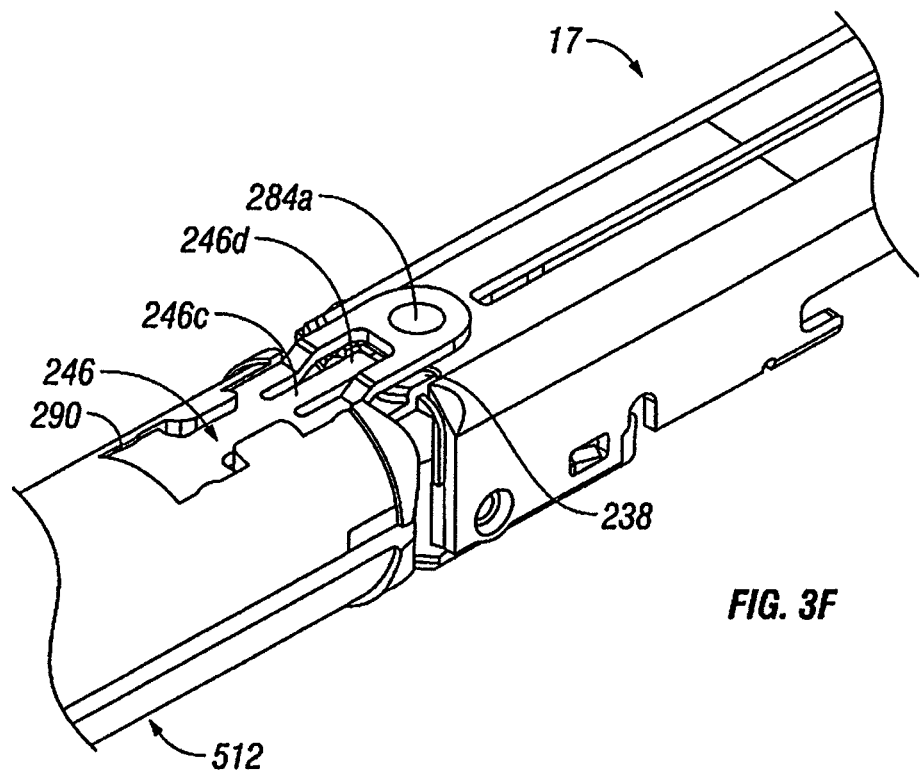
FIG. 3F is a side perspective view from below of the distal end of the proximal body portion, the mounting assembly and the proximal end of the tool assembly of the DLU of the surgical instrument with the tool assembly in its non-articulated position.
Figure 3G:
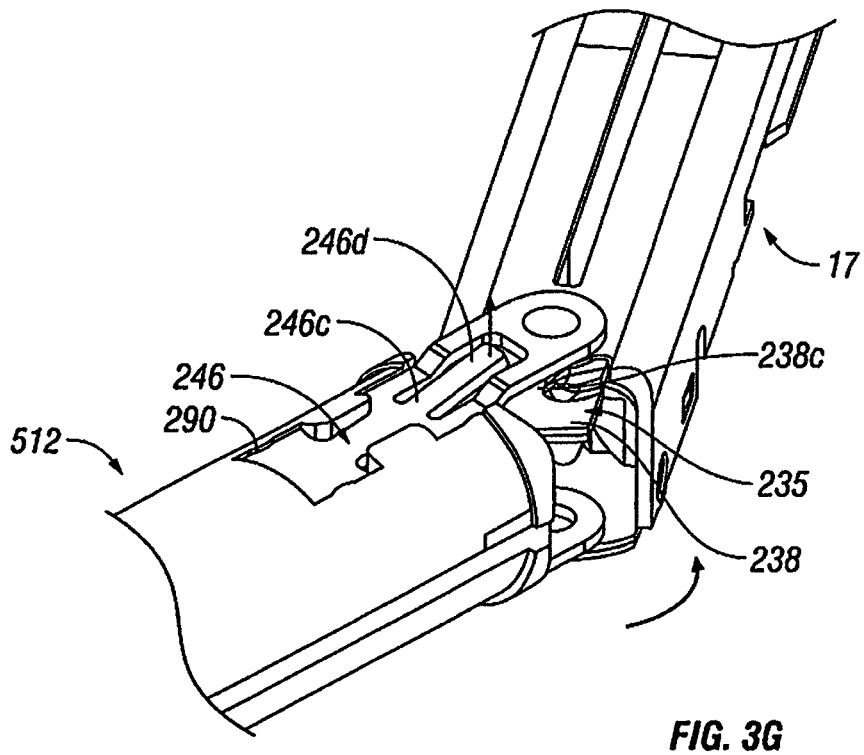
FIG. 3G is a side perspective view from below of the distal end of the proximal body portion, the mounting assembly and the proximal end of the tool assembly shown in FIG. 3F with the tool assembly moving to an articulated position.

As illustrated in FIGS. 3D-3G, when distal end 246d of spring arm 246c of coupling member 246 is positioned in recesses 236b of upper mounting portion 236, spring arm 246c retains mounting assembly 235 in a non-articulated position. Spring arm 246c retains mounting assembly 235 in its non-articulated position until a predetermined force sufficient to deflect spring arm 246c from recess 236b is applied to effect articulation of mounting assembly 235 and tool assembly 17. Spring arm 247c is similarly retained in recess 238c to retain the position of mounting assembly 235. When the predetermined force is applied to the mounting assembly 235 and tool assembly 17, spring arms 246c, 247c will spring outwardly from recesses 236b and 238c, as shown in FIGS. 3E and 3G, to permit pivotal movement of mounting assembly 235 (and, thus, tool assembly 17) in relation to the distal end of proximal body portion 200 of the DLU 16.

As discussed above, spring arms 246c, 247c and recesses 236b and 238c maintain tool assembly 17 in its non-articulated position until a predetermined force has been applied to mounting assembly 235 to disengage spring arms 246c, 247c from recesses 236b and 238c of mounting assembly 235. It is envisioned that the spring arms/recesses could be incorporated into any articulating surgical device including staplers, graspers (See FIG. 3H), powered sealing devices, e.g., RF sealing devices, etc. Further, although two spring arms/recesses are shown, a single spring arm can be provided. Moreover, the articulating tool assembly need not for part of a DLU but rather can be supported directly on the distal end of a surgical instrument. For example, the mounting assembly can be removably or irremovably secured to the tool assembly and secured directly to the distal end of a surgical instrument.

With reference to FIG. 3, upper housing half 250 and lower housing half 252 are contained within an outer sleeve 251 of body portion 200. Body portion 251 includes a cutout 251a dimensioned to receive a projection or projection 250a formed on upper housing half 250. The positioning of projection 250a within cutout 251a prevents axial and rotational movement of upper and lower housing halves 250 and 252 within outer sleeve 251 of body portion 200. In one embodiment, projection 250a has a substantially rectangular configuration having a greater axial dimension than lateral dimension. The greater axial dimension provides increased surface area for preventing rotation of upper and lower housing halves 250 and 252 within sleeve 251. A proximal portion 250b of projection 250a is ramped. Ramped proximal portion 250b allows sleeve 251 to be slid over projection 250a as upper and lower housing halves 250 and 252 are positioned within sleeve 251. It is envisioned that projection 250a may assume other configurations, e.g., circular, square, triangular, etc., and still achieve its intended function. Further, projection 250a can be repositioned anywhere along upper housing half 250 or, in the alternative, be positioned on lower housing half 252 or partly on each housing half 250 and 252.

The proximal end or insertion tip 193 of upper housing half 250 includes engagement nubs 254 for releasably engaging the distal end of a surgical instrument in a bayonet type fashion. Housing halves 250 and 252 define a channel 401 for slidably receiving axial drive assembly 212 therein. A first articulation link 256 is dimensioned to be slidably positioned within a slot 402 formed between upper and lower housing halves 250 and 252. A pair of H-block assemblies 255 are positioned adjacent the distal end of housing portion 200 and adjacent the distal end of axial drive assembly 212 to prevent outward buckling and bulging of drive assembly 212 during articulation and firing of surgical instrument 500. Each H-block assembly 255 includes a flexible body 255a which includes a proximal end fixedly secured to body portion 200 and a distal end fixedly secured to mounting assembly 235.

A retention member 288 is supported on engagement section 270 of axial drive assembly 212. Retention member 288 includes a pair of fingers 288a which are releasably positioned within slots or recesses 252a formed in lower housing half 252. In operation, when SULU 16 is attached to a surgical instrument and axial drive assembly 212 is actuated by applying a predetermined force to an actuation member 516 of the surgical instrument 500 (FIG. 10), axial drive assembly 212 is advanced distally to move drive assembly 212 and retention member 288 distally. As retention member 288 is advanced distally, fingers 288a are forced from recesses 252a to provide an audible and tactile indication that the surgical instrument has been actuated. Retention member 288 is designed to prevent inadvertent partial actuation of DLU 16, such as during shipping, by maintaining axial drive assembly 212 at a fixed position within DLU 16 until a predetermined axial force has been applied to axial drive assembly 212.

Axial drive assembly 212 includes an elongated drive beam 266 including a distal working head 268 and a proximal engagement section 270. In one embodiment, drive beam 266 is constructed from multiple stacked sheets of material. Engagement section 270 includes a pair of resilient engagement fingers 270a and 270b which mountingly engage a pair of corresponding retention slots formed in drive member 272. Drive member 272 includes a proximal porthole 274 configured to receive distal end of a control rod 520 (FIG. 10) of a surgical instrument when the proximal end of DLU 16 is engaged with the body portion 412 of a surgical instrument 500.

With reference to FIGS. 1 and 5-9, an articulation mechanism 400 is shown which includes an articulation knob 402, an articulation spindle 404, and a second articulation link 406. The articulation spindle 404 provides a mechanical interface between the articulation knob 402 and the second articulation link 406. The articulation spindle 404 includes a cylindrical member 412 having a first diameter and a flange 414 disposed on top of the cylindrical member 412 (See FIG. 7). The flange 414 extends laterally from the cylindrical member 412 and has a second diameter which is larger than the first diameter of the cylindrical member 412.

The articulation spindle 404 is rotatably housed within a housing block 410 which is integrally formed with the housing of the handle 510. The housing block 410 includes a recessed portion 420 having a first diameter and a stepped portion 422 having a second diameter. During assembly, when the articulation spindle 404 is inserted into the housing block 410, the cylindrical member 412 and the flange 414 mechanically interface with the recessed portion 420 and stepped portion 422 respectively due to corresponding first and second diameters of these components.

The articulation knob 402 is mounted on top of the articulation spindle 404 about a knob interface member 416 which extends upwardly from a top surface of the flange 414 and is preferably formed integrally therewith. This allows for rotational motion of the articulation knob 402 to be translated to the rotational motion of the articulation spindle 404. The interface member 416 has a polygonal (e.g., rectangular) shape configured for transferring torque exerted by the knob 402 to the articulation spindle 404. The knob 402 may be integrally formed with the articulation spindle 404. A cover 405 having an opening for the interface member 416 to pass therethrough is disposed on top of the articulation spindle 404 and below the articulation knob 402. The cover 405 encloses the components of the articulation mechanism 404 within the housing block 410. The cover 405 may be secured to the housing block 410 via a variety of conventional mechanisms known to those skilled in the art such as screws, rivets, etc.

The second articulation link 406 extends in a longitudinal direction within the body portion 512 and includes a second articulation finger 424 at a distal end thereof. The articulation finger 424 is configured to interface with a first articulation finger 427 disposed at a proximal end of the articulation link 256. This allows for translation of longitudinal movement of the second articulation link 406 to the first articulation link 256 which then forces articulation of the tool assembly 17. More specifically, the upper mounting portion 236 includes an articulation pivot member 236c which extends downwardly from the upper mounting portion 236. The first articulation link 256 includes a bore 256a for receiving the pivot member 236c. The pivot member 236c interconnects the upper and lower mounting portions 236, 238 with the first articulation link 256 therebetween as the pivot member 236c passes through the bore 256a. Longitudinal motion of the first articulation link 256 forces the upper and lower mounting portions 236 and 238 to rotate about the pivot member 284 thereby articulating the tool assembly 17.

The longitudinal motion of the first and second articulation links 256 and 406 is imparted via the rotational motion of the articulation spindle 404. The second articulation link 406 mechanically interfaces with the articulation spindle 404 via a link interface member 418 which extends downwardly from a bottom surface of the cylindrical member 412 of articulation spindle 404. The second articulation link 406 includes an articulation slit 426 which extends laterally across the second articulation link 406. The interface member 418 is positioned off center on the bottom surface of the cylindrical member and is received within the slit 426. During rotation of the articulation spindle 404, the interface member 418 is rotated around the center thereof. Since the slit 426 is dimensioned at its width to substantially fit around the interface member 418, the interface member 418 only travels in a lateral direction therein and the longitudinal component of the rotational motion of the interface member 418 is translated to the second articulation link 406.

The articulation spindle 404 also includes a mechanism for limiting maximum articulation angle of the tool assembly 17. More specifically, the articulation spindle 404 includes a guide member 430 extending downwardly from a bottom surface of the flange 414. The guide member 430 is configured to mechanically interface with an arcuately shaped guide channel 432 which is disposed within a top surface of the stepped portion 422. The guide member 430 moves within the channel 432 and limits the rotational range of the articulation spindle 404 to the length of the channel 432.

The articulation mechanism 400 also provides the user with tactile feedback and means to control the rotation of knob 402 and, hence, the articulation of tool assembly 17 in predetermined increments. The flange 414 includes a series of notches 434 set in an outer circumferential surface thereof. The notches 434 are set at a predetermined length apart from each other and are configured to interface with a locking mechanism 435. The locking mechanism 435 includes a spring loaded plunger 436 disposed within a recess 438 in housing block 410, with the plunger 436 facing generally perpendicularly with respect to the outer circumferential surface of the flange 414. Another elastic mechanism providing pressure thereon may be used in lieu of a spring as understood by those skilled in the art. The plunger 436 due to the spring therein is pushed against the outer surface of the flange 414 and as the articulation spindle 404 is rotated, the notches 434 are passed across the plunger 436. When one of the notches 434 is aligned with the plunger 436, the plunger 436 is forced into the notch 434 via the spring. This allows for indexing the rotational position of the spindle 404 with an articulation position of the tool assembly 17. The tip of the plunger 436 and the notches 434 are preferably formed of complementary shapes (e.g., conical, tapered edges, etc.) to allow for ease of mating and disengaging upon application of sufficient torque to the articulation spindle 404.

In certain embodiments, the articulation spindle 404 includes five notches 434 positioned along the circumferential outer surface of the flange 414. A middle notch 434 coincides with a 0° articulation position and neighboring notches 434 correspond to ±22.5° and ±45° positions respectively for a resulting total articulation angle of 90°. The arc length of the guide channel 432 also corresponds to the maximum desired articulation of 90°, such that when the knob 402 is rotated to the maximum articulation positions of ±45°, the guide channel 432 limits the movement of the guide member 430 beyond those points and consequently limits rotation of the articulation spindle 404.

When the articulation knob 402 is rotated in either direction, clockwise or counterclockwise, the articulation spindle 404 initially requires a minimum amount of torque to overcome the locking mechanism 436. Upon reaching the first neighboring notch 434, the plunger 436 is forced therein and locks the articulation spindle 404 temporarily in place providing tactile feedback to the user. As the articulation spindle 404 is rotated, the rotational motion of the interface member 418 is translated into longitudinal motion of the second articulation link 406 via the slit 426 as the interface member 418 travels therein. Longitudinal motion of the articulation link 256 is translated to longitudinal motion of the articulation pivot member 236c on mounting assembly 235, which forces the tool assembly 17 to articulate about the pivot member 284. Rotating the articulation spindle 404 to the final position of 45°, locks the tool assembly 17 in place due to the guide member 430 of the articulating spindle 404 encountering the end of the guide channel 432 and the plunger 436 interfacing with the furthest notch 434. To unlock the tool assembly 17, the knob 402 is turned in the opposite direction, traversing through other notches 434 and the neutral axial plane (e.g., 0°) of the middle notch 434. The rotational range of the knob 402 is ±95° which corresponds with articulating the tool assembly 17 between ±45° positions.

Those skilled in the art will appreciate that the articulation spindle 404 may include any number of notches 434 disposed at various intervals depending on the desired articulation angles and/or positions. It is further to be understood that the articulation angles and maximum rotation ranges disclosed with respect to the articulation mechanism 400 are illustrative.

Figure 9:
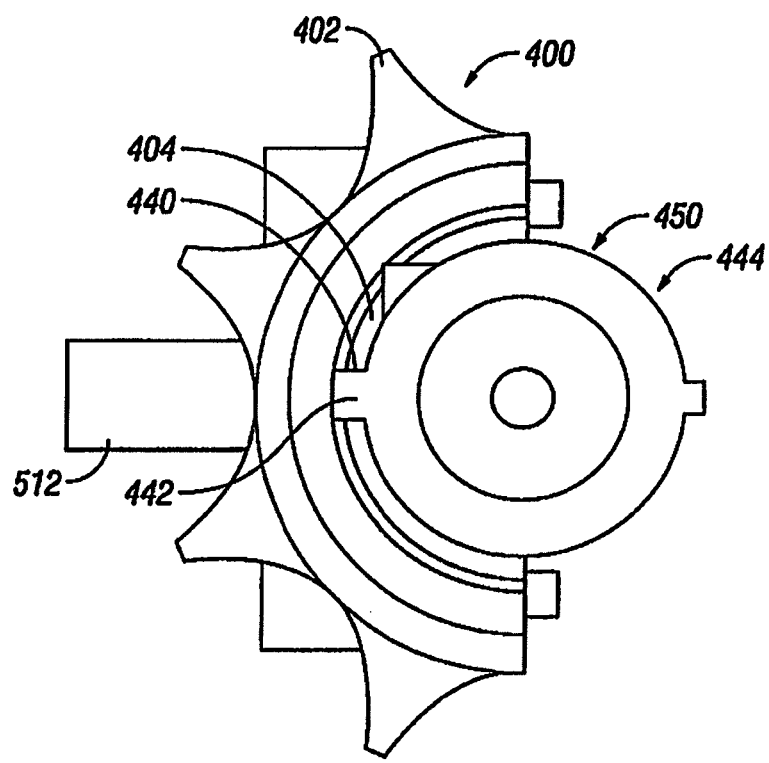
FIG. 9 is a cross-sectional view taken along section line 9-9 in FIG. 5.

Referring to FIG. 9, shows a cross-sectional view of a sensing mechanism 450 operatively associated with the articulation mechanism 400 and positioned within the housing block 410. The sensing mechanism 450 includes a cap sensor 444 having a nub portion 442 configured to be received within a slot 440 of the articulation spindle 404. The cap sensor 444 is adapted to sense the type of a disposable loading unit 16 engaged with the body portion 512. In the first position as shown in FIG. 9, the cap sensor 444 is configured to interface with the articulation spindle 404 and prevent articulation thereof if the nub portion 442 is recessed within the slot 440. The articulating disposable loading unit 16 has an extended insertion tip 193 (FIG. 1A). When the articulating DLU is inserted into the distal end of body portion 512 of surgical instrument 500, insertion tip 193 moves proximally into engagement with cap sensor 444 to force the cap sensor 444 and nub portion 442 proximally and out of the slot 440. With nub portion 442 positioned outside the slot 440, the articulation spindle 404 is free to move rotatably to effect articulation of surgical instrument 500. A non-articulating disposable loading unit does not have an extended insertion tip. As such, when a non-articulating disposable loading unit is inserted, cap sensor 444 is not retracted proximally a sufficient distance to move the nub portion 442 from slot 440. Thus, articulation spindle 404 is prevented from moving rotatably by nub portion 442 of the cap sensor 444 which is positioned in slot 440 and the articulation spindle 404 is locked in its neutral position. Another type of sensing mechanism is described in a commonly-owned U.S. Pat. No. 5,865,361 entitled "Surgical Stapling Apparatus" the contents of which are hereby incorporated herein in their entirety by reference.

It will be understood that various modifications may be made to the embodiments disclosed herein. For example, the DLU may be configured to receive an insertion tip of surgical instrument in contrast to that disclosed. Therefore, the above description should not be construed as limiting, but merely as exemplifications of preferred embodiments. Those skilled in the art will envision other modifications within the scope and spirit of the claims appended hereto.

What is claimed is:

1. An articulation mechanism for articulating a surgical tool assembly, the articulation mechanism comprising:
  a housing defining a longitudinal axis, the housing including a recessed portion having a first diameter, and a stepped portion having a second diameter;
  an articulation spindle rotatably disposed within the housing and having an interface member, the articulation spindle including:
    a cylindrical member having a bottom surface, the interface member extending downwardly from the bottom surface; and
    a flange disposed on top of the cylindrical member and extending radially outward from the cylindrical member, wherein the cylindrical member mechanically interfaces with the recessed portion and the flange mechanically interfaces with the stepped portion; and
  a first articulation link having a proximal and a distal end configured to be coupled to a proximal end of a second articulation link of a surgical tool assembly, the proximal end of the first articulation link defining a slit and the interface member movably received in the slit, wherein translational movement of the interface member through the slit effects an axial movement of the first articulation link and the slit thereof along the longitudinal axis.

2. The articulation mechanism according to claim 1, wherein the stepped portion of the housing defines a guide channel therein having an arcuate shape, the articulation spindle having a guide member extending downwardly from the flange and configured for movable receipt in the guide channel.

3. The articulation mechanism according to claim 2, wherein the guide channel has an arc length corresponding to a maximum rotation of the articulation spindle.

4. The articulation mechanism according to claim 1, wherein the slit of the first articulation link defines an axis disposed perpendicular to the longitudinal axis of the housing, such that the interface member is configured to move perpendicular to the longitudinal axis of the housing.

5. The articulation mechanism according to claim 1, further comprising a plunger disposed in the housing and biased to engage the articulation spindle.

6. The articulation mechanism according to claim 5, wherein the articulation spindle includes a cylindrical outer surface having a plurality of notches defined therein, each notch of the plurality of notches configured to releasably receive the plunger.

7. The articulation mechanism according to claim 6, wherein each of the plurality of notches is configured to index a rotational position of the articulation spindle with an articulation position of a surgical tool assembly.

8. The articulation mechanism according to claim 7, wherein at least two of the plurality of notches corresponds to maximum articulating positions of a surgical tool assembly.

9. The articulation mechanism according to claim 6, wherein the plunger extends perpendicularly relative to an outer circumferential surface of the articulation spindle.

10. The articulation mechanism according to claim 1, wherein the housing and the articulation spindle are configured to limit a rotational range of the articulation spindle.

11. The articulation mechanism according to claim 1, wherein the interface member is positioned off center on the bottom surface.

12. The articulation mechanism according to claim 1, further comprising an articulation knob non-rotatably coupled to the articulation spindle for rotating the interface member.

13. The articulation mechanism according to claim 1, further comprising a cap sensor axially movable within the housing, the cap sensor having a nub portion configured to be selectively received within a slot of the articulation spindle, wherein the cap sensor is axially movable between a distal position, in which the nub portion is received within the slot of the articulation spindle to resist rotation of the articulation spindle, and a proximal position, in which the nub portion of the cap sensor is disposed outside of the slot of the articulation spindle to allow the articulation spindle to rotate.

14. The articulation mechanism according to claim 1, wherein the slit is enclosed.

* * * * *